United States Patent [19]

Creech et al.

[11] Patent Number: 5,733,478
[45] Date of Patent: Mar. 31, 1998

[54] METHOD AND COMPOSITION FOR REDUCING THE DEGRADATION RATE OF AGROCHEMICALS IN STORAGE

[75] Inventors: David C. Creech; James P. Glatzhofer; Shane A. Wyatt, all of Yuma, Ariz.

[73] Assignee: Gowan Company, Yuma, Ariz.

[21] Appl. No.: 718,898

[22] Filed: Sep. 24, 1996

[51] Int. Cl.$^6$ .................. G09K 15/32; G09K 3/00; N01N 59/26; N01N 57/00
[52] U.S. Cl. .................. 252/400.21; 252/382; 252/384; 424/601; 514/109; 514/126
[58] Field of Search .................. 252/384, 382, 252/400.21; 424/607; 514/126, 109

[56] References Cited

U.S. PATENT DOCUMENTS

| | | | |
|---|---|---|---|
| 3,214,333 | 10/1965 | Peacock | 167/22 |
| 4,892,732 | 1/1990 | Parconagian et al. | 424/409 |
| 4,940,699 | 7/1990 | Itoh et al. | 514/114 |
| 5,335,449 | 8/1994 | Beatty | 47/48.5 |
| 5,435,939 | 7/1995 | Narayanan | 252/312 |
| 5,599,803 | 2/1997 | Hainrihar et al. | 514/70 |

*Primary Examiner*—Sharon Gibson
*Assistant Examiner*—Deanna Baxam
*Attorney, Agent, or Firm*—Antonio R. Durando

[57] ABSTRACT

A method for reducing the rate of degradation of stored agrochemicals, particularly pesticides, is provided which essentially involves incorporating a stabilizing compound into the agrochemical in preparation for storage, with the stabilizing compound selected from the group consisting of a diol and a triol. In the preferred embodiment, a pesticide having the active ingredient METASYSTOX® has an improved shelf life with the addition of about 2 parts by weight of propylene glycol to about 25 parts by weight of METASYSTOX®.

15 Claims, No Drawings

METHOD AND COMPOSITION FOR REDUCING THE DEGRADATION RATE OF AGROCHEMICALS IN STORAGE

BACKGROUND OF THE INVENTION

1. Field of the Invention

The present invention relates to the storage of agrochemicals, and, more particularly, to the reduction of the degradation rate of pesticides by the incorporation of a diol or triol additive.

2. Description of the Prior Art

Agricultural chemicals, such as pesticides and concentrates thereof, are widely used by agricultural operations to control the incidence of insect populations among crops. The journey of agricultural chemicals (hereinafter "agrochemicals") from manufacture to use can be rather lengthy in both time and distance. Typically, manufacturers provide agrochemicals in concentrated form to formulation/packaging facilities, which then dilute the agrochemicals to a useful concentration and package the agrochemicals in secure containers in preparation for transport and handling. The packaged agrochemicals may be exposed to high temperatures for extended periods while being transported and stored for ultimate end use in an agricultural operation.

It is known that certain agrochemicals begin to degrade with exposure to high temperature. For example, META-SYSTOX R® thermally degrades, with its rate of degradation being directly proportional to its temperature. META-SYSTOX R® is the trade designation for O,O-dimethyl-S-2-(ethylsulfinyl)ethylphosphorothioate, which is an active ingredient for the insecticide that is commercially available under that name from The Gowan Company of Yuma, Ariz. Other examples of pesticidal compounds known to degrade upon exposure to heat are azinphos methyl and dimethoate, also respectively known as O,O-dimethyl-S-4-oxo-1,2,3-benzotriazin-3(4H)-yl methyl phosphorodithioate and O,O-dimethyl-S-(N-methylcarbamoylmethyl) phosphorodithioate, the former of which is commercially available from the Bayer Company under the trade designation GUTHION®.

Present storage containers for hazardous chemicals, while being substantially improved to withstand impact and shock, are not capable of sufficiently insulating their cargo from high temperatures during extended storage and handling periods. Most hazardous and toxic chemicals are presently stored and transported in metal drums or, for smaller quantities, plastic containers. It is also known to package such chemicals in water-soluble bags contained within an all-enclosing flexible container or bag. Such "bag-in-a-bag" packaging systems typically comprise an inner water-soluble bag containing the hazardous chemical, with the inner bag being inserted into an outer bag made of flexible polymeric material.

While certain packaging systems such as the "bag-in-a-bag" approach may offer a fairly high degree of insulation, the fact remains that no practical amount of packaging insulation can prevent heat-induced degradation of susceptible compounds in high temperature environments over long periods of time. Further, regardless of the type of container, it is cost prohibitive and impractical to provide external cooling during transport and handling. In general, it is estimated that pesticides may not reach their end-use following manufacture for a period of up to three years.

Therefore, a need exists for a cost-effective and easily-implemented means to reduce the rate of heat-induced degradation of packaged agrochemicals, particularly METASYSTOX R® and other organo-phosphate pesticides.

SUMMARY OF THE INVENTION

In accordance with the invention, a method of reducing the rate of thermally-induced degradation of a pesticide during its storage is provided, along with the composition of pesticides having improved stability throughout storage. Essentially, a reduction in thermally-induced degradation of pesticides is achieved by incorporating a stabilizing compound, namely a diol or triol, into the pesticide composition prior to placing the pesticide into a storage container. More specifically, the pesticide composition provided herein comprises (a) at least one organo-phosphate active ingredient; (b) at least one solvent; and (c) at least one stabilizing compound selected from the group consisting of a diol and a triol.

Without the present stabilizing compound, pesticides having organo-phosphate active ingredients, such as METASYSTOX®, have a limited shelf life because of the tendency of such active ingredients to degrade upon exposure to higher temperatures. The incorporation of a diol or triol compound into the pesticide composition effectively retards the rate of degradation, thereby significantly extending the shelf life of treated pesticides. The diol and triol compounds that serve as stabilizing agents are widely available, and adding these stabilizing agents to pesticides is easily accomplished.

Therefore, the present method offers a cost-effective, easily-implemented solution to the problem of heat-induced degradation of pesticides.

DETAILED DESCRIPTION OF THE INVENTION

The invention described herein is directed to a method of reducing the rate of degradation of pesticides occurring during their storage. The method comprises incorporating a stabilizing compound into the agrochemical in preparation for storage, with the stabilizing compound selected from the group consisting of a diol and/or a triol. The invention is directed particularly at improving the stability of META-SYSTOX R®, the preferred stabilizing compounds being propylene glycol and glycerin, in that order. Thus, a heat-resistant pesticide composition is provided that exhibits an improvement in shelf-life deriving from the incorporation of a stabilizing diol or triol compound into the composition.

Before specifically addressing the components of the present pesticide composition, it is noted that the purity of all components is that employed in normal commercial practice for agricultural chemicals. Weight percents represent percent of total agrochemical composition, unless otherwise indicated.

Pesticides are available in different physical forms. For example, pesticides are commercially available in the form of a solid such as powders, dust, or granules, and in the form of a liquid. Regardless of the form taken by the pesticide, it is the stability of the active ingredient in the pesticide composition which primarily determines the shelf life of the pesticide. The present invention addresses the heat-initiated decay of active ingredient(s) in a pesticide.

Examples of active ingredients in pesticides that degrade upon exposure to heat include organo-phosphate compounds such as METASYSTOX R®, azinphos methyl, and dimethoate. METASYSTOX R® is the trade designation for an organo-phosphate compound that is generically known as O,O-dimethyl-S-2-(ethylsulfinyl)ethyl phosphorothioate, which is commercially available in the U.S.A. from The Gowan Company. A similar, diethyl composition (O,O-diethyl-S-2-(ethylsulfinyl)ethyl phosphorothioate) is also available as a pesticide and is characterized by the same reactive properties. The structure of METASYSTOX R® is as follows:

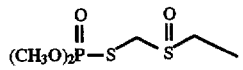

In typical commercial form, METASYSTOX R® is manufactured at about 90% grade. The remaining 10% is typically represented by the sulfide starting material for METASYSTOX R® and a sulfoxide. These compounds, which are respectively illustrated below, undergo degradation in a similar fashion to METASYSTOX R®:

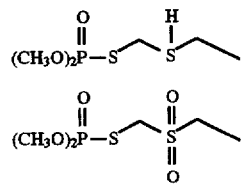

As explained above, METASYSTOX R® thermally degrades, with its rate of degradation being directly proportional to its temperature. Generally speaking, the time period of decay for METASYSTOX R® is measured in months and years for cooler temperatures (i.e., room temperature or less) versus weeks and months for warmer temperatures (e.g., 120° F. (50° C.)).

Two different decomposition reactions occur depending upon whether the solution has a relatively high or low pH. For example, the degradation of METASYSTOX R® proceeds to the following structure at a pH of 5 or lower:

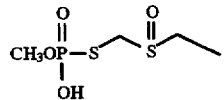

When the pH is 9 or higher, METASYSTOX R® degrades into the following thiol structure, with the rate of degradation being much faster than if the pH were less than about 5:

Although the invention is herein described primarily with reference to METASYSTOX R®, it is contemplated that, in addition to the structure of METASYSTOX R® employing a dimethyl group, as illustrated above, the practice of the invention would also benefit its diethyl homolog and other similar compounds.

Typically, METASYSTOX R® technical grade is commercially available as a liquid concentrate comprising about 50 to 57 wt % METASYSTOX R® and the balance a solvent, such as methylisobutyl ketone. This liquid concentrate is diluted to the concentration of choice (typically a low viscosity solution of thin consistency) prior to packaging for shipment and end-use as a pesticide. In the practice of the invention, the active ingredient is preferably present in the pesticide composition between the range of 15 to 35 wt %.

The preferred composition of an as yet unstabilized pesticide employing METASYSTOX R® comprises (a) about 50 wt % of the liquid concentrate; (b) about 26 wt % additional methylisobutyl ketone; (c) about 14 wt % xylene range solvent; and (d) about 10 wt % ten mole nonyl phenol surfactant. Therefore, assuming that the manufacturing concentrate comprises 50 wt % METASYSTOX R®, the pesticide composition actually comprises about 25 wt % of this active ingredient. It is noted that the practice of the invention is not limited to a particular solvent system or pesticide composition: rather, the addition of a stabilizing compound benefits the active ingredient of the pesticide regardless of its form or associated pesticide components.

The methylisobutyl ketone component of the preferred pesticide composition is commercially available, for example, from Ashland Chemical, Inc. of Columbus, Ohio. It is a flammable liquid that serves to uniformly disperse the METASYSTOX R® into a solution. Alternative solvents that may be suitably employed are propylene carbonate and monochloro benzene.

The xylene range solvent of the preferred pesticide composition is commercially available, for example, from Exxon Chemical Company under the trade designation AROMATIC 100 Solvent as a clear colorless liquid. The purpose of the xylene range solvent is to dilute the concentration of the active ingredient to a convenient volume. (The active ingredient of a pesticide is used as a weight per area, but is measured by volume.) Since the xylene range solvent is less expensive than methylisobutyl ketone, it is preferred for purposes of dilution.

The ten mole nonylphenol surfactant of the preferred embodiment is commercially available, for example, from Rhône-Poulenc of Cranbury, N.J., under the trade designation Igepal CO-630, which is generically known as nonylphenoxypoly(ethyleneoxy)ethanol, branched. Igepal CO-630 is a free flowing viscous liquid having a molecular weight of about 615, and it serves as an emulsifier to render the solvent emulsified in water. It also reduces the interfacial tension between the components of the pesticide once added to a spray tank in end-use agricultural operations.

It is contemplated that various other additives may be incorporated in the pesticide solution to achieve certain desired qualities, such as other surfactants, dispersants, thickeners, antifoaming agents, antifreezing agents, gelling agents, dyes, and perfumes, among others.

In accordance with the tenets of the present invention, a stabilizing agent is incorporated into the pesticide composition to retard the heat-induced decomposition of the active ingredient. Specifically, we found that the addition of a relatively small amount of a diol or triol into the pesticide composition significantly reduces the rate of decomposition of an organo-phosphate active ingredient, such as METASYSTOX R®. Examples of diols that may be suitably employed in the practice of the invention include ethanediol (more commonly known as ethylene glycol); propanediol (i.e., propylene glycol); and diethylene glycol; while an example of a suitable triol is glycerin (i.e., 1,2,3-propanetriol). Preferably, propylene glycol is employed in the practice of the invention. Commercially-available propylene glycol typically contains both 1,2-propylene glycol and 1,3-propylene glycol (also known as 1,2-propane diol and 1,3-propane diol, respectively) and both forms are considered substantially equally effective.

Without subscribing to any particular theory, it is postulated that the diol and triol stabilizing agents reduce the decomposition rate of organo-phosphate active ingredients by tying up water in the pesticide composition, or retarding its decomposition by steric hindrance.

It is noted that not all polyols are effective as stabilizing agents in the practice of the invention. For example, Igepal CO-630 is a polyol and is not believed to be effective in stabilizing an organo-phosphate active ingredient.

For the preferred heat-susceptible pesticide composition provided above containing about 25 wt % METASYSTOX®, the amount of stabilizing agent preferably employed in the practice of the invention is about 2 wt %, for an active ingredient:stabilizing agent ratio of about 25:2 by weight. This ratio is preferred for pesticide compositions having a concentration of METASYSTOX R® within ±10% of 25 wt %, or within the range of about 22.5 to 27.5 wt %, but it has been tested with positive results with compositions having METASYSTOX R® concentrations as high as about 50%. Employing the stabilizing agent at about 0.5 wt % or less is substantially ineffective, while employing substantially more than about 2 wt % results in diminishing returns. (Tests were run successfully with propylene glycol concentrations as high as 25 wt %, but the cost outweighs the benefit at concentration greater than about 5 wt %.)

Assuming an approximately 50 wt % liquid concentrate of METASYSTOX R® and an approximately 50% dilution thereof, the following represents the preferred pesticide composition in the practice of the invention: (a) about 49 to 53 wt % of the liquid concentrate (with the balance adjusted as necessary in the remaining ingredients); (b) about 25 wt % additional methylisobutyl ketone; (c) about 14 wt % xylene range solvent; (d) about 10 wt % ten mole nonyl phenol surfactant; and (e) about 2 wt % propylene glycol.

It is important in the practice of the invention to be mindful of the presence of water in the pesticide composition. Water may be introduced into the pesticide composition by various means, such as by introducing atmospheric humidity thereinto during mixing, transferring, and performing other formulation steps. Although the preferred pesticide composition may contain a certain amount of water, the composition is somewhat hygroscopic. Therefore, the water content must be restricted. In fact, a water content above 0.8 wt % of the pesticide composition overwhelms the beneficial effect of adding the stabilizing agent to control the decomposition of the active ingredient METASYSTOX R®.

EXAMPLES

The efficacy of incorporating a diol or triol compound into a pesticide to reduce the degradation rate of pesticides in storage in accordance with the invention was demonstrated by the following experiments.

Four formulations were prepared in accordance with the practice of the invention, and their chemical stability compared to a formulation without the stabilizing agent (i.e., the "control"). The control pesticide had the following formulation: (a) about 25 wt % METASYSTOX R®; (b) about 51 wt % methylisobutyl ketone; (c) about 14 wt % xylene range solvent; and (d) about 10 wt % ten mole nonyl phenol surfactant. About 2 wt % of a stabilizing compound was added to the above control composition to formulate four different pesticide preparations in accordance with the invention.

Although the components of the pesticide composition may be introduced in any order, the control pesticide and four additional pesticide compositions were formulated by adding the components in the order listed above to a stainless steel vessel. The resulting mixture was then stirred with a propeller mixer. The pesticide compositions were also neutralized with ethylene diamine and filtered.

The five formulations were placed in separate sealed glass bottles and maintained at 122° F. (50° C.) throughout testing using an electronically-controlled forced air laboratory oven. The chemical stability of the METASYSTOX R® was measured weekly for each of the five formulations at the outset, and then again at 4, 8, and 11 weeks. Table 1 below compares the measured chemical stabilities:

TABLE 1

Chemical Stability of METASYSTOX R ® at 122° F. (50° C.)

| | Initial | Four Weeks | | Eight Weeks | | Eleven Weeks | |
|---|---|---|---|---|---|---|---|
| Additive | Assay | Abs.[1] | %[2] | Abs. | % | Abs. | % |
| None | 29.8 | 29.8 | 0 | 28.8 | 3.4 | 26.9 | 9.7 |
| 2 wt % glycerin | 30.8 | 31.2 | 1.3 | 31.2 | 1.3 | 30.0 | 2.6 |
| 2 wt % ethylene glycol | 31.5 | 31.4 | 0.3 | 30.6 | 2.9 | 29.5 | 6.3 |
| 2 wt % propylene glycol | 28.3 | 28.3 | 0 | 28.4 | — | 28.2 | 0.4 |
| 2 wt % diethylene glycol | 30.8 | 31.2 | — | 30.7 | 0.3 | 28.9 | 6.2 |

[1]Absolute measurement of chemical stability, ± 2%.
[2]Percent degradation in chemical stability as calculated from initial assay Clearly, the addition of a diol or triol in accordance with the invention bolsters the chemical stability of a pesticide having 25 wt % METASYSTOX R® at the stated temperature. While the control pesticide exhibited almost 10% degradation in chemical stability after 11 weeks, the four pesticides having a diol or triol experienced decline ranging from 0.4 to 6.3%, with the least decline being exhibited with the addition of propylene glycol as the stabilizing compound. It is noted that the longer the simulated storage period, the more evident was the protective effect of the stabilizing compound. While a storage period of four weeks produced relatively little distinction between the control pesticide and the pesticides prepared in accordance with the invention, the chemical stability of the stabilized pesticides clearly evidenced improvement compared to the control after eleven weeks.

The foregoing demonstrated that the incorporation of diols and triols such as ethylene glycol, propylene glycol, diethylene glycol, and glycerin effectively reduces heat-induced degradation of METASYSTOX R®. The method and compositions disclosed herein for reducing heat-induced degradation of pesticides by the incorporation of a diol or triol stabilizing agent are expected to find commercial use in the agricultural chemical manufacturing and packing industries.

Once the pesticide composition contains an appropriate amount of stabilizing agent in accordance with the practice of the invention, the stabilized pesticide is considered essentially prepared for packaging. The type of packaging employed does not form part of the present invention. However, it is contemplated that the stabilized pesticide composition formulated in accordance with the present invention will preferably be packaged in a bag-in-a-bag containment system, which is well known in the art (see U.S. Pat. No. 5,330,047.

The bag-in-a bag containment system generally comprises an inner water-soluble bag contained in an outer water-insoluble bag. Therefore, a pesticide so packaged can be easily handled by farmers, e.g., by ripping open the outer bag and tossing the inner water-soluble bag in water in a spraying tank prior to spraying the pesticide. The preferred pesticide of the present invention is a substantially non-aqueous solution that is partly water-soluble but does not substantially dissolve or permeate the inner water soluble bag. Typical materials used for the inner water-soluble bag are water soluble polymer films such as polyethylene oxide, methylcellulose, and poyvinylalcohol, while typical materials for the outer bag include polymeric materials such as polypropylene, nylon, polyethylene (metalized or non-metalized) or polyester. Preferably, there is a certain amount of air or inert material in the space between the outer and inner bags to enhance the shock resistance of the containment system.

Therefore, when employing a bag-in-a bag containment system, one would fill the inner water-soluble bag with the stabilized pesticide prepared in accordance with the present invention. The filled inner water-soluble bag is then closed and placed inside the outer bag, which is finally sealed.

Should the stabilized pesticide formulated in accordance with the practice of the invention be stored in a bag-in-a-bag containment system, its acidity would become a concern. Specifically, the product may be too acidic for the inner water-soluble bag—for example, the preferred composition of the stabilized pesticide has a pH of about 2.4. To counter this, ethylene diamine may be added to the pesticide to react with the acid which then forms a precipitate that may then be filtered off. In this manner, the acidity is reduced to acceptable levels, a pH of about 6 to 7 being necessary (a pH of 6.5 is optimal), without leaving ionic residues in the product that may initiate premature degradation of the active ingredient or negatively affect its quality. Optimally, ethylene diamine is added to the concentration of about 0.1 wt % of the pesticide. The addition of a small amount of ethylene diamine for this purpose has been shown to have no effect on the chemical stability of the active ingredient in the pesticide.

It is noted that certain other additives may be employed to improve the performance of the bag-in-a-bag containment system for pesticides formulated in accordance with the invention, or for any material so stored for that matter. Beneficial additives include those serving to lubricate and make easier the removal of the inner bag from the outer bag. For example, we discovered that the introduction of a small amount of glycerin or other plasticizer material in the space between the inner water soluble bag and the outer water insoluble bag can be used advantageously for several independent purposes. The first is to lubricate the interspace between the bags, so that the inner bag can be easily slipped into and out of the outer bag even when very little space or tolerance exists between them; that is, when the two bags have approximately the same dimensions. Tests have shown that the seal zone of the outer bag is not adversely affected by the addition of glycerin or other lubricating material.

Another purpose is to provide a reservoir of plasticizer material to prevent or retard the embrittlement of the water-soluble inner bag which is normally associated with such two-bag systems. The inner product, a water-free composition, tends to strip plasticizer from the film constituting the water soluble bag. By providing a source of replacement of such plasticizer from the reservoir created between the two bags, the water-soluble film is prevented from becoming brittle and will last much longer under normal storage conditions. Finally, we found that the fluid introduced between the two bags has a humectant effect on the water soluble film constituting the inner bag, which results in retaining the film's softness for an extended period of time during transportation and storage.

We found that these advantages were achieved not only with glycerin, but also with diols such as ethylene glycol, propylene glycol, dipropylene glycol, diethylene glycol, and diacetone alcohol; with polyols such as polyethylene glycol, sorbitol, mannitol, and sucrose; with water solutions of trimethylol propane; with emulsions of seed oils; and with dioctyl phthalate. These materials were applied directly or, if necessary to decrease their viscosity or to reduce them to liquid form, by first dissolving them in water or other solvent, and then by spraying them or roller coating them over the inside wall of the outer bag, or by dipping the inner bag into them, before the inner bag is introduced into the outer bag. Similar advantages would be expected by coating either surface with a lubricant by any other means.

Thus, there has been disclosed herein a method and pesticide composition which slows the rate of degradation of pesticides during storage by incorporating a stabilizing compound, namely a diol or triol, into the pesticide composition. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A pesticide having resistance to thermal degradation, said pesticide comprising:
    (a) at least one organo-phosphate active ingredient selected from the group consisting of O,O-dimethyl-S-2-(ethylsulfinyl)ethyl phosphorothioate and O,O-diethyl-S-2-(ethylsulfinyl)ethyl phosphorothioate;
    (b) at least one solvent; and
    (c) at least one stabilizing compound selected from the group consisting of a diol and a triol.

2. The pesticide of claim 1 wherein said at least one organo-phosphate active ingredient is present in said pesticide at a concentration ranging from about 15 to 35 wt % of said pesticide.

3. The pesticide of claim 1 wherein the weight ratio of said at least one active ingredient to said at least one stabilizing compound in said pesticide is about 25:2.

4. The pesticide of claim 1 wherein said at least one solvent is selected from the group consisting of methyl-isobutyl ketone, xylene range solvent, propylene carbonate, monochloro benzene, and mixtures thereof.

5. The pesticide of claim 1 wherein said pesticide further comprises a surfactant.

6. The pesticide of claim 5 wherein said surfactant is a nonyl phenol surfactant.

7. The pesticide of claim 1 wherein said diol is selected from the group consisting of ethylene glycol, propylene glycol, and diethylene glycol, and wherein said triol is glycerin.

8. The pesticide of claim 1 wherein said at least one stabilizing compound comprises propylene glycol.

9. The pesticide of claim 1 wherein said pesticide is a fluid.

10. The pesticide of claim 1 wherein said at least one stabilizing component is propylene glycol present in said pesticide at a concentration greater than 0.5 wt % of said pesticide.

11. The pesticide of claim 1 wherein said at least one stabilizing component is propylene glycol present in said pesticide at a concentration greater than 0.5 wt % of said pesticide.

12. The pesticide of claim 1 wherein said at least one organo-phosphate active ingredient is present in said pesticide at a concentration ranging from about 15 to 35 wt % of said pesticide; said at least one stabilizing component is propylene glycol present in said pesticide at a concentration greater than 0.5 wt % of said pesticide; said at least one solvent is selected from the group consisting of methyl-isobutyl ketone, xylene range solvent, propylene carbonate, monochloro benzene, and mixtures thereof; and said diol is selected from the group consisting of ethylene glycol, propylene glycol, and diethylene glycol, and wherein said triol is glycerin.

13. The pesticide of claim 12 wherein the weight ratio of said at least one active ingredient to said at least one stabilizing compound in said pesticide is about 25:2.

14. The pesticide of claim 12 wherein said pesticide further comprises a surfactant.

15. The pesticide of claim 12 wherein said pesticide is a fluid.

* * * * *